United States Patent
Pagniéz et al.

(10) Patent No.: US 7,094,952 B1
(45) Date of Patent: Aug. 22, 2006

(54) METHOD FOR OBTAINING TRANSGENIC PLANTS EXPRESSING A PROTEIN WITH ACTIVITY PRODUCING HYDROGEN PEROXIDE BY TRANSFORMATION BY AGROBACTERIUM RHIZOGENES

(75) Inventors: Michel Pagniéz, Pibrac (FR); René Grison, Escalquens (FR); Alain Toppan, Cornebarrieu (FR)

(73) Assignee: Biogemma, Paris (FR)

( * ) Notice: Subject to any disclaimer, the term of this patent is extended or adjusted under 35 U.S.C. 154(b) by 0 days.

(21) Appl. No.: 09/821,463

(22) PCT Filed: Oct. 8, 1999

(86) PCT No.: PCT/FR99/02412

§ 371 (c)(1),
(2), (4) Date: Jun. 12, 2001

(87) PCT Pub. No.: WO00/22148

PCT Pub. Date: Apr. 20, 2000

(30) Foreign Application Priority Data

Oct. 9, 1998 (FR) .................................. 98 12704

(51) Int. Cl.
C12N 15/82 (2006.01)
C12N 15/87 (2006.01)
C12N 5/10 (2006.01)
C07H 26/04 (2006.01)

(52) U.S. Cl. ...................... 800/294; 800/278; 800/298; 435/419

(58) Field of Classification Search ................ 800/278, 800/298, 294; 536/23.1; 435/419
See application file for complete search history.

(56) References Cited

FOREIGN PATENT DOCUMENTS

| EP | 262972 | 4/1988 |
|---|---|---|
| EP | 687730 | 12/1995 |
| EP | 716147 | 6/1996 |
| WO | 92/01792 | 2/1992 |
| WO | 94/13790 | 6/1994 |
| WO | 97/37012 | 10/1997 |
| WO | 98/51806 | 11/1998 |

OTHER PUBLICATIONS

Simpson, et. al., A disarmed binary vector from Agrobacterium tumefaciens functions in Agrobacterium rhizogenes, Plant Mol. Biology, vol. 6, pp. 403-415, 1986, (Applicant's IDS).*

Zhang, et. al., Germin-like oxalate oxidase, a hydrogen peroxide producing enzyme, accumulates in barley attacked by the powdery mildew fungus, The Plant Journal, vol. 8, pp. 139-145, 1995.*

( Buchanan, et al. Biochemistry & Molecular Biology of Plants (2000) American Society of Plant Physiologists, Rockville Md 20855, pages p. 32-33).*

Hansen (Recent advances in the transformation of plants, Trends in Plant Science, vol. 4, No. 6, Jun. 1999, pp. 226-231, see pp. 228, 229 and 230).*

Webb et al. (1994), " Expression of GUS in primary transformants and segregation patterns of GUS, TL- and TR-DNA in the T1 generation of hairy root transformants of Lotus corniculatus", Chem. Abstracts, vol. 121(23), No. 276934.

Zhang et al. (1995), "Germin-like oxalate oxidase, a H2O2-producing enzyme, accumulates in barley attacked by the powdery mildew fungus", Plant J., 8(1), pp. 139-145.

Hatamoto et al. (1990) "Recovery of morphologically normal transgenic tobacco from hairy roots co-transformed with Agrobacterium rhizogenes and a binary vector plasmid", *Plant Cell Rep.*, pp. 88-92.

Boulter etal. (1990) "Transformation of Brassica Napul L. (oilseed rape) using Agrobacterium tumefaciens and Agrobacterium rhizogenes-a comparison", *Plant Sci.*, pp. 91-99.

Simpson et al., (1986), "A disarmed binary vector from Agrobacterium tumefaciens functions in Agrobacterium rhizogenes", Plant Mol. Biol., 6, pp. 403-415.

Shahin et al. (1986), "Transformation of cultivated tomato by a binary vector in Agrobacterium rhizogenes:transgenic plants with normal phenotypes harbor binary vector T-DNA", *Theor. Appl. Genet.*, 72(6), pp. 720-777.

Grison et al. (Field tolerance to fungal pathogens of Brassica-Napus constitutively expressing a chimeric chitinase gene, Database Scisearch Online, AN 96:394736.

* cited by examiner

*Primary Examiner*—Elizabeth McElwain
*Assistant Examiner*—Georgia Helmer
(74) *Attorney, Agent, or Firm*—Dennison, Schultz & MacDonald

(57) ABSTRACT

The subject of the present invention is a method for obtaining transgenic plants expressing a protein with $H_2O_2$ producing activity, which comprises the following steps of:

(a) transforming plant cells with *Agrobacterium rhizogenes* containing a vector carrying a gene encoding a protein producing $H_2O_2$ in a context which allows its expression in the plant;

(b) selecting the transformants which contain and express this gene, by a peroxidase-based colorimetric test;

(c) regenerating the plants from the roots selected and monitoring the expression of the plantlets obtained by a peroxidase-based colorimetric test;

(d) sorting according to phenotype and optionally carrying out the molecular analysis of the progeny of the transgenic plants, allowing the selection or the confirmation of transgenic plants obtained containing only the transgene and not the T-DNA specific to *A. rhizogenes*.

Application: Obtaining of transgenic plants

18 Claims, 1 Drawing Sheet

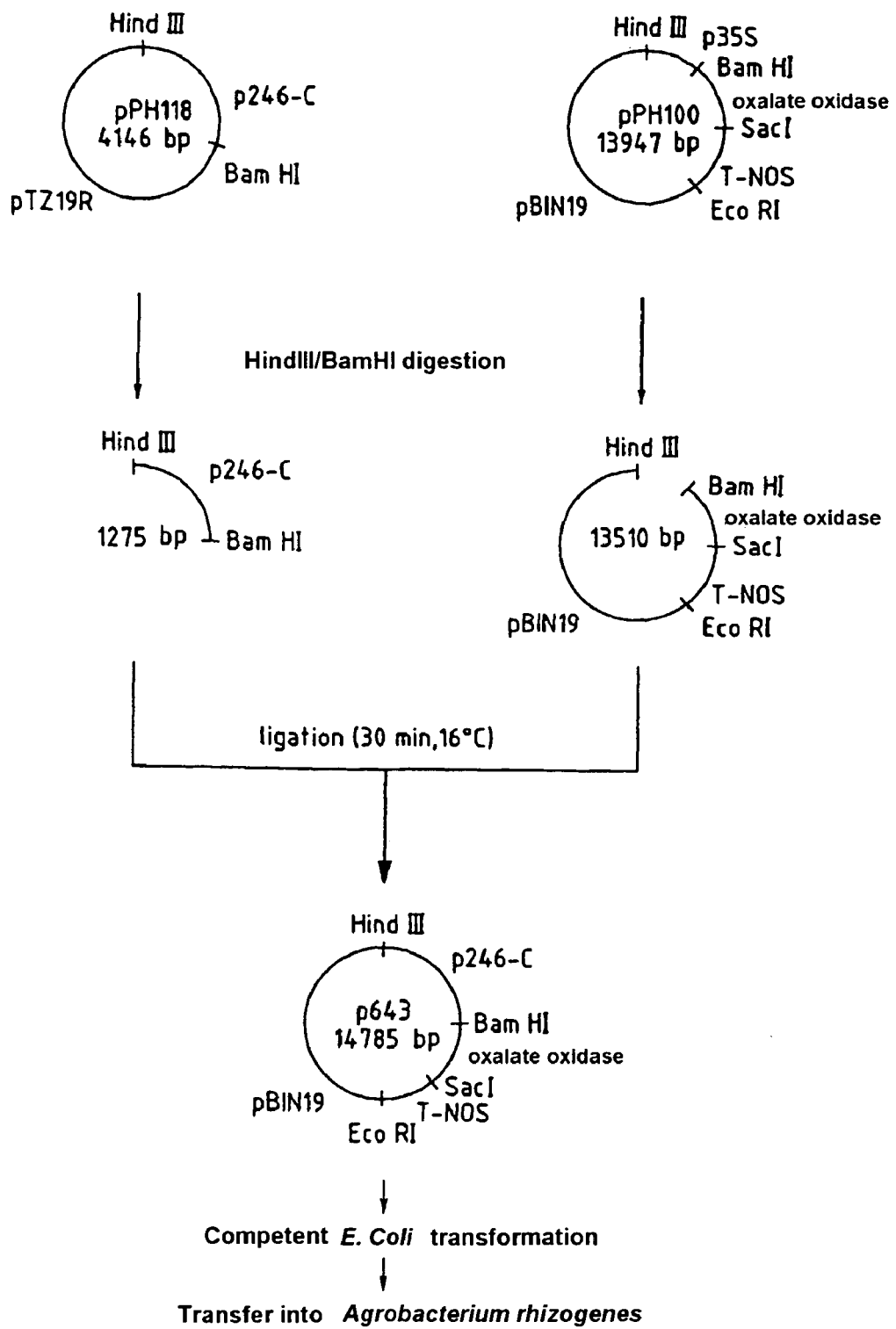

SEQUENCE LISTING

<160> NUMBER OF SEQ ID NOS: 4

<210> SEQ ID NO 1
<211> LENGTH: 4
<212> TYPE: PRT
<213> ORGANISM: Unknown Organism
<220> FEATURE:
<223> OTHER INFORMATION: Description of Unknown Organism:targeting
      peptide

<400> SEQUENCE: 1

Lys Asp Glu Leu
 1

<210> SEQ ID NO 2
<211> LENGTH: 6
<212> TYPE: PRT
<213> ORGANISM: Unknown Organism
<220> FEATURE:
<223> OTHER INFORMATION: Description of Unknown Organism:targeting
      peptide

<400> SEQUENCE: 2

Ser Glu Lys Asp Glu Leu
 1               5

<210> SEQ ID NO 3
<211> LENGTH: 4
<212> TYPE: PRT
<213> ORGANISM: Unknown Organism
<220> FEATURE:
<223> OTHER INFORMATION: Description of Unknown Organism:targeting
      peptide

<400> SEQUENCE: 3

His Asp Glu Leu
 1

<210> SEQ ID NO 4
<211> LENGTH: 1332
<212> TYPE: DNA
<213> ORGANISM: Nicotiana tabacum

<400> SEQUENCE: 4 ccttttcga ttctaatcca atcaattcaa cagtgtaagg tgaagcagtc aatttaaagg      60
aaggccttta aattctaaaa tattgtactt ttcctgcgct tctaaaagtg aacgacaaag    120
aaaaaatagt tattcttgaa cttaatattg tacaatagga taaatttaa ctatctataa    180 aaagagaaca aaaccttaat ctcttcaaaa taatattata agaagtaaca taattgtcaa    240
atgaaataca cataagaagc acataaattt aaatgccgta ttaaacttac agtatactat    300
agcggaagtt ggcttgataa aggaacgctg aggagagtag ccgatggtga aacactaaca    360
tcaagtgcaa agaaagaaa aactgaaaac agaagatgaa tgtttgaagt gggtaaaaga    420
ttacttaaaa gataggtttg gttaacaaat gattgtgact gttacgaagc agtgtgaacc    480
gttgggactt ttaatattct tcggcagaag aacattgctc tttccacgta tgtagtcttt    540
gtctacttgt agttttttt aatttaaatt aaataagtta attagagaaa taataagaag    600
gatattttag taattcaact tttaactttt aggtttccca cttataatat aatatagata    660 tagtttttt taatttaaat taaataagtt aattagagaa ataataagaa ggatatttta    720
gtaattcaac ttttaacttt tagggtttcc acttataata taatatagat atagatatag    780

```
atatagatat agataaagat atatagatat agatagataa tatagatgga tgagtcattg      840
gcgataaagt gaggattgtt tcatttttgt tattaaaaac ttactactcc ttaaatataa      900
aatatgattc cttttaaaaa agaaatagaa taaaaataaa gataaaacac taaaaataaa      960
ttaattgtct agacaaaatc taccgttcac ctcaattaat acacatcccc gtccacatca     1020
tgaagtagct agcacaagcg tacagatcag ttgaaagaag aaaagggtcc agtcctaaat     1080
atccaaatgt tcatgaaagg aggacaactt agttttttct actagaaaga atattttgac     1140
gaatttcgtt cacattggca tgctttaatt atattaagta gtctttcttg gaaaagaagt     1200
atttgcaata tcaaaccaaa tcttcccatt acgcaagcaa tgacatctaa gcaaatatat     1260
atcactataa atagtactac taatgttcaa tgacttttat aagcactaca tatatatact     1320
caaacaaaaa ga                                                          1332
```

METHOD FOR OBTAINING TRANSGENIC PLANTS EXPRESSING A PROTEIN WITH ACTIVITY PRODUCING HYDROGEN PEROXIDE BY TRANSFORMATION BY AGROBACTERIUM RHIZOGENES

This application is a 371 of PCT/FR99/02412, filed on Oct. 8, 1999.

The invention relates to the field of the genetic transformation of plants by *Agrobacterium rhizogenes*, combined with the use of a gene encoding a protein with hydrogen peroxide producing activity and in particular oxalate oxidase.

The subject of the present invention is a method for obtaining transgenic plants, characterized in that it uses transformation by *Agrobacterium rhizogenes* combined with visual sorting of the transformation events, based on colouring, which is simple to carry out and is rapid, of the transformed roots expressing the transgene.

Since the first field trials, thus out of confinement, of transgenic plants took place in 1986, the use of a gene for resistance to an antibiotic as selection gene has been the subject of numerous reviews (Casse-Delbart and Tepfer, Biofutur, (1990), June; 56–59, as well as Bryant and Leather, Tibtech, (1992), 10, 274–275). Although the possibilities of transmission of genes from the transgenic plant to soil bacteria had not been demonstrated, the use of antibiotic resistance genes is very badly perceived by some authors (Heinemann, TIG, (1991), 7, 181–185).

Numerous substitutes for the kanamycin resistance gene have been proposed (Ratner, Bio-Technology, (1989)-7, 337–341) but the majority of these genes for resistance to another antibiotic or to a herbicide lead to similar objections or to technical difficulties of implementation.

The use of oxalate oxidase as selection gene offers an alternative to the previous systems. Demonstrated in some plants, this protein is capable of degrading oxalic acid, which is a phytotoxin produced during infection by numerous plant pathogens.

A first application of oxalate oxidase has been the production of transgenic plants resistant to pathogens of the genus *Sclerotinia* (WO 92/14824).

Patent application WO 94/13790 describes a novel use of oxalate oxidase as a replacement for kanamycin, in a system of selective pressure of the transformants. According to the method described in WO 94/13790, only the transformants (calluses) containing the oxalate oxidase gene survive a specific sublethal dose of oxalic acid, present in the medium. However, the preparation of the selection media (dose of oxalic acid, calcium chelators) is cumbersome and constraining.

Up until now, oxalate oxidase was used coupled with the toxic agent, oxalic acid, in a selective pressure perspective, whereas in the method of the present application it is used simply as a marker for visual sorting of the transformants. Nevertheless, this protein did not appear a priori a good candidate as a marker since it was highly expressed in plants infected by a pathogen, hence there was a high risk of distorting the results (false positives, for example). Furthermore, the teaching of patent application WO 94/13790 did not encourage persons skilled in the art to use a colorimetric test for the selection of the transformants since such a test makes it possible to select individualized events (transformed cells) and not events dispersed in a heterogeneous material such as the callus, derived from the transformation by *Agrobacterium tumefaciens* and containing, in the form of a mixture, transformed cells and nontransformed cells.

The present invention therefore provides a method for obtaining transgenic plants which is advantageous in that it removes the technical constraints of the method described above by the combination of the characteristics of *Agrobacterium rhizogenes* and a protein with $H_2O_2$ producing activity. In particular, the inventors exploit the formation of roots which is induced by *Agrobacterium rhizogenes* and the phenotype of the transformants (crinkled leaves, plagiotropic roots, shorter internodes) in combination with the production of $H_2O_2$ (hydrogen peroxide) by the protein for the development of a novel system for selecting homogeneous transformants. In this system, the hydrogen peroxide produced is revealed in the presence of peroxidase, to produce coloration of the samples of transformed roots.

BRIEF DESCRIPTION OF THE DRAWING

FIG. 1: Construction of vecto p643.

According to a first aspect, the subject of the present invention is a method for obtaining transgenic plants which comprises the following steps of:

(a) transforming plant cells with *Agrobacterium rhizogenes* containing a vector carrying a gene encoding a protein with $H_2O_2$ producing activity;

(b) selecting the transformants which contain and express this gene, by a peroxidase-based calorimetric test;

(c) regenerating the plants from the roots selected and monitoring the expression of the plantlets obtained by a peroxidase-based colorimetric test;

(d) sorting according to their phenotype and optionally validating by molecular analysis the progeny of the transgenic plants obtained, allowing the selection or the confirmation of plants containing only the transgene and not the T-DNA specific to *Agrobacterium rhizogenes*.

The peroxidase-based colorimetric test used in steps b) and c) of the method of the invention consists in incubating a sample of plant tissues collected in the presence of a medium containing a substrate for the protein with $H_2O_2$ producing activity, such as for example oxalic acid, and in revealing the formation of $H_2O_2$ with the aid of peroxidase in the presence of an appropriate substrate whose oxidation is accompanied by a change of color. The concentration of substrate in the incubation medium is not critical since the system of visual sorting on the sample according to the present invention does not require the survival of the cells, while that is the case for the selective "vital" sorting of the transformed cells which is described in application WO 94/13790. In the present case, the substrate concentration is advantageously a saturating concentration so that the $H_2O_2$ producing activity is favored and the products easily revealed with peroxidase, in the form of an intense blue color. The teaching of application WO 94/13790 does not indicate the use of an oxalic acid concentration greater than the exemplified sublethal dose, which is 3 mM; however, it is found that the optimum substrate concentrations for visual sorting are well above this critical concentration. By way of example, the oxalic acid concentrations may be within a broad range going from 5 to 50 mM and preferably from 10 to 20 mM, in particular 15 mM.

The calorimetric test performed in step b) of the method is advantageously carried out on a root sample. It may also be carried out on the incubation liquid medium, advantageously after decontamination of the explants (elimination of the *agrobacteria*), knowing that the protein, such as oxalate oxidase, can diffuse from the site where it is expressed. Likewise, revealing on the blot left by the transformed explants on an agar medium or on a membrane is also possible.

The calorimetric test performed in step c) of the method may be carried out on a sample of plant tissue from the regenerated plants.

According to the invention, the plant cells are transformed with *Agrobacterium rhizogenes* containing a recombinant DNA comprising a gene encoding a protein with $H_2O_2$ producing activity in a context which allows its expression in the plant. *Agrobacterium rhizogenes*, which is described for example by Tepfer, Physiologica Plantarium, (1990), vol. 79 p. 140–146, is a bacterium capable of infecting said plant cells by allowing the integration, into the genome thereof, of DNA sequences of interest initially contained in the *Agrobacterium rhizogenes* T-DNA. Indeed, the transformation of plant cells uses a binary system (Watson in Genetic engineering of crop plants, Butterworths, 1990) comprising two vectors: the first being the pRi specific to *Agrobacterium rhizogenes* and responsible for the formation of the transformed roots; the second vector, of the binary type (Bevan, Nuc. Acid. Res. (1984), 12: 8711), contains the gene encoding the protein with $H_2O_2$ producing activity and preferably oxalate oxidase; this gene will be called hereinafter selection gene.

The protein encoded by the selection gene is a protein with $H_2O_2$ producing activity. By way of example of such proteins, there may be mentioned NADPH oxidases, oxalate oxidases, amine oxidases, glucose oxidases and the like (Bolwell and Wojtazek, Plant Mol. Plant Pathol., (1998), 51, 347). The genes encoding these proteins can be used for the purposes of the invention.

Preferably, a gene will be used which encodes a protein with oxidase activity, such as for example oxalate oxidase from barley (marketed by Boehringer, ref. 567698), from sorghum (Pundier, Phytochemistry, (1991), 30, 4, 1065) or from the moss *Mnium menziesii* (Laker et al, Clinical Chemistry, (1980), 26, 7, 827).

A protein with oxalate oxidase activity which is particularly appreciated is wheat germin, whose sequence has been described by Dratewka-Kos, J. Biol. Chem, (1989), 264, 4896) and Lane, J. Biol. Chem. (1991), 266, 10461). Taking into account the degeneracy of the genetic code, a large number of nucleotide sequences encoding oxalate oxidase exist which can also be used for the purposes of the invention.

The recombinant DNA comprises the gene encoding the protein with $H_2O_2$ producing activity, flanked by means necessary for its expression, in particular a promoter, a transcription terminator, and optionally a sequence encoding a targeting peptide of plant origin.

The promoter is preferably a strong constitutive promoter, for example the cauliflower mosaic virus 35S promoter.

Alternatively, it is possible to use the promoter of the gene encoding the plant elongation factor, such as the EF-1α promoter described in patent application WO 90/02172 or by Axelos et al. Plant Mol. Biol., (1989), 219: 1–2, 106. It is also possible to use a tissue-specific promoter, a promoter active during a specific stage of development of the plant, or a promoter inducible under stress situations, for example following a heat shock, wounding or the interaction between the plant and parasites (Kuhlemeier et al., Ann. Rev. Plant Physiol., (1987), 38: 221), if the selection phase requires the expression of the $H_2O_2$ producing gene under these situations.

Among the other transcription promoters which can be used, there may be mentioned in particular:

the CaMV $^{35}$S double constitutive promoter (35Sdp), described in the article by Kay et al., Science, (1987), 236: 4805;

the superpromoter chimeric promoter SPP (Ni M et al., Plant J., (1995), 7: 661) consisting of the fusion of a triple repeat of a transcriptional activator of the *Agrobacterium tumefaciens* octopine synthase gene promoter, of a transcriptional activator of the mannopine synthase gene promoter and of the *Agrobacterium tumefaciens* mannopine synthase promoter;

the rice actin promoter followed by the rice actin intron (RAP-RAI) contained in the plasmid pAct1-F4 described by McElroy et al., (Mol. Gen. Genet., (1991), 231: 150).

It is also possible to use promoters specific to the seed, in particular:

the barley HMGW (High Molecular Weight Glutenine) promoter described by Anderson et al., T.A.G., (1989), 77, 689–700;

the promoter of the corn γ-zein gene (Pγ-zein) contained in the plasmid pγ63, and allowing expression in the albumen of corn seeds, described by Reina et al., Nucleic Acid Research, (1990), 18, 6426;

the radish cruciferin gene promoter PCRU allowing the expression of the sequences associated solely with the seeds (or grains) of the transgenic plant obtained; this promoter is described by Depigny-This et al., Plant. Mol., Biol., (1992), 20, 467–479;

The PGEA1 and PGEA6 promoters corresponding to the noncoding 5' region of the genes for the storage protein in seeds, GEA1 and GEA6, respectively, from *Arabidopsis thaliana* (Gaubier et al., Mol. Gen. Genet (1993), 238, p. 409–418, and allowing specific expression in the seeds.

A terminator sequence is used which comprises polyadenylation sites, and which can be isolated from plant genes or from genes expressed in plants, such as for example the *Agrobacterium tumefaciens* nopaline synthase gene terminator (Depicker et al., J. Mol. Appl. Genet (1982), 1, 561–573).

Among the sequences encoding a targeting peptide of plant origin, which can be used in the context of the invention, there may be mentioned:

the nucleotide sequence of 69 nucleotides encoding the prepeptide (signal peptide) of 23 amino acids of sporamine A in sweet potato, allowing the entry of the recombinant polypeptides into the secretory system of the transformed plant cells;

the nucleotide sequence of 42 nucleotides encoding the N-terminal propeptide for vacuolar targeting of 14 amino acids of sporamine A in sweet potato, allowing the accumulation of the recombinant polypeptides in the vacuoles of the transformed plant cells;

the sequence of 111 nucleotides encoding the prepropeptide of 37 amino acids of sporamine A consisting, from the N-terminal end to the C-terminal end, of the 23 amino acids of the abovementioned signal peptide followed by the 14 amino acids of the abovementioned propeptide, this prepropeptide allowing the entry of recombinant polypeptides into the secretory system and their accumulation in the vacuoles of the transformed plant cells according to the invention, the three abovementioned sequences being described by Murakami et al., Plant Mol. Biol., (1986), 7, 343–355 and by Matsuoka et al. in Proc. Natl. Acad. Sci. USA, (1991), 88, 834–838;

the barley lectin carboxy-terminal propeptide described in particular by Schroeder et al. in Plant Physiol., (1993), 101, 451–458 and by Bednarek et al., in The Plant Cell, (1991), 3, 1195–1206;

and the PRS (Pathogenesis Related Protein) of Cornelissen et al. Nature, (1986), 321, 531–532 allowing secretion.

There may also be mentioned, among the sequences encoding a targeting peptide, those encoding the peptides Lys-Asp-Glu-Leu (KDEL) (SEQ ID NO:1); Ser-Glu-Lys-Asp-Glu-Leu (SEKDEL) (SEQ ID NO:2); and His-Asp-Glu-Leu (HDEL) (SEQ ID NO:3), and allowing targeting into the endoplasmic reticulum.

A bacterium, for example of the species *Escherichia coli*, which contains the recombinant DNA defined above with the means allowing its replication can serve for the cloning of this recombinant DNA. A bacterium capable of infecting a plant with transfer of genetic material, *Agrobacterium rhizogenes*, which contains this DNA in a context allowing its replication, will serve to transform plant cells.

The invention also relates to a plant cell, characterized in that it is transformed with the recombinant DNA defined above. This plant cell may be derived from a major crop species, such as for example corn, soybean, wheat, barley, rape, sunflower and pea, or from a culinary species such as lettuce, melon, tomato, cabbage, onion and corn, preferably sweet corn. Species which are particularly appreciated are rape *Brassica napus*, sunflower *Helianthus annuus*, tobacco *Nicotiana tabacum*, cauliflower *Brassica oleracea* and tomato *Lycopersicon esculentum*. Preferably, the invention relates to species not endogenously expressing oxalate oxidase.

The invention also relates to a plant or a plant part, characterized in that it contains the recombinant DNA defined above and in that it was selected by visualization of the enzymatic activity of the protein with $H_2O_2$ producing activity using a peroxidase-based colorimetric test, applied to the roots derived from in vitro culture or to plant tissues taken from the whole plants. The transgenic plants are regenerated directly from the roots or organs selected by the peroxidase-based calorimetric test.

The plant parts defined according to the invention comprise in particular the hypocotyls, scapes of flowers, petioles and preferably cotyledons. The expression plant part is also understood to mean the cells cultured in vitro or the cells of said plant.

According to another aspect of the invention, the recombinant DNA sequence encoding a protein with $H_2O_2$ producing activity is used to select plant cells transformed with a sequence of interest.

Thus, the invention also relates to a method for obtaining transgenic plants expressing a gene of interest, other than that for the protein with $H_2O_2$ producing activity, combined with a gene encoding an $H_2O_2$ producing protein, which comprises the following steps of:

(a) transforming plant cells with *Agrobacterium rhizogenes* containing a recombinant DNA comprising both a gene encoding the $H_2O_2$ producing protein and a gene encoding a protein of interest in a context allowing their expression in the plant;

(b) selecting the transformants which contain the gene encoding the protein of interest by a peroxidase-based calorimetric test;

(c) regenerating plants from selected transformants and monitoring the expression of the plantlets obtained by a peroxidase-based calorimetric test;

(d) sorting according to the phenotype and optionally carrying out a molecular analysis of the progeny of the transgenic plants in order to select or confirm the plants containing only the transgene and not the T-DNA specific to *A. rhizogenes*.

(e) purifying, where appropriate, the protein of interest produced.

This novel system for immediate visualization on the root is particularly advantageous in the case where the gene of interest is expressed at a late stage of development or in a vegetative organ other than that on which the selection is made or else if it is difficult to demonstrate. It can, for example, be used to select transformation events relating to a gene of interest placed under the control of a promoter specific to the seed or specifically expressed in the green tissues.

The sequence of interest may be any DNA sequence of agronomic or industrial interest. For example, it may be involved in a given metabolic pathway, in particular that of oils, starches, proteins, amino acids, lignin, components of the cell wall or in the pathway for resistance to pathogens. This sequence of interest may also be used in sense or antisense.

It may also be, for example, an advantageous regulatory sequence. It may also be a sequence encoding a protein of interest or a precursor thereof. By way of example of sequences encoding a protein of interest, there may be mentioned the sequences encoding lipases.

According to a preferred embodiment of the invention, the sequence of interest confers on the plants resistance to pathogenic agents, such as fungi, bacteria, as well as arthropods, in particular insects, and nematodes.

Such a sequence of interest may be, for example, a sequence encoding a protein with endochitinase activity or a precursor thereof. It is indeed known, as described in patent application WO 92/01792, that such a protein has a phytoprotective effect because it is capable of degrading chitin, a polysaccharide polymer consisting of N-acetylglucosamine units linked by β-1,4 linkages, which is an important structural compound of the wall of most pathogenic fungi, of the exoskeleton of arthropods, in particular insects, and of the external envelope of eggs and cysts of nematodes.

A sequence of interest encoding a protein with endochitinase activity or a precursor thereof is that described in patent application WO 92/01792, incorporated by reference.

Another sequence encoding a protein with endochitinase activity or a precursor thereof is that of the *Aphanocladium album* chitinase described in patent application EP-A1-531 218, incorporated by reference.

The invention also relates to the plant cells, characterized in that they are transformed by the recombinant DNA defined above, namely the recombinant DNA comprising a gene encoding a protein with $H_2O_2$ producing activity and a gene encoding a protein of interest as well as the means necessary for their expression. Said means are the same as those defined above. These plant cells may be obtained from the species of major crops or from the culinary species indicated above.

The invention also relates to a plant or plant part, characterized in that it expresses the protein of interest described above, with the means necessary for the expression of the gene encoding a protein capable of producing $H_2O_2$ and in particular oxalate oxidase. This plant or plant part is selected by a calorimetric test for revealing the $H_2O_2$ formed on the roots derived from cultivation in vitro or from greenhouse plants. The transgenic plants are regenerated directly from the roots expressing the transgene which are selected by the calorimetric test.

The plant parts are as defined above.

The invention will be illustrated with the aid of the examples described below.

In this experimental part, the clone gf-2.8 of the wheat germin described by Lane et al., J. Biol. Chem., (1991), 226, 10461 is used.

A large part of the whole of the techniques below, which are well known to persons skilled in the art, is set out in detail in the works of Sambrook et al.: "Molecular Cloning: a Laboratory Manual", published in 1989 by the publishers Cold Spring Harbor Press in New York (2nd edition), and in the work of Gelvin et al.: "Plant Molecular Biology Manual", published in 1988 by the publishers Kluwer Academics.

EXAMPLES

Example 1

Transformation of Plants by the Gene for Wheat Germin and Selection of the Transformants by a Colorimetric Test on the Root 1-1 Obtaining of Transgenic Rape a) Transformation Vectors According to a first embodiment of the invention, the sequence encoding the wheat germin is ligated to the cauliflower mosaic virus $^{35}$S promoter sequence and to the *Agrobacterium tumefaciens* NOS terminator sequence, before being inserted into the binary vector pBIN19 (Bevan, Nucl. Acid, Res., (1984), 12, 8711–8721) according to the procedure described in Section 2 of application WO94/13790, incorporated by reference. The vector obtained, called pPH100, is cloned into the *E. coli* HB101 strain (Clontech).

According to another embodiment of the invention, the procedure was carried out in the same manner as above using the promoter sequence of the gene encoding the promoter of the Elongation Factor EF-1α isolated from *Arabidopsis thaliana* (Axelos et al, Plant Mol Biol, (1989), 219: 1-2, 106) in place of the 35S promoter sequence. The new vector, called p631, is cloned into the *E. coli* HB 101 strain.

The promoter sequence may also be the inducible promoter sequence described in patent application WO 94/21793 and carried by the vector pPH118 described in Example 3 below.

b) Transfer into *Agrobacterium rhizogenes*

The transfer of the plasmids described above is carried out according to the freeze-thaw method described by Gelvin et al. in Plant Molecular Biology Manual mentioned above, with the *Agrobacterium rhizogenes* A4 strain described by Guerche et al. in Mol. Gen. Genet., (1987), 206, 382.

The bacteria are plated on Petri dishes containing 100 mg/l of rifampicin and 25 mg/l of kanamycin. The colonies which then form are subcultured several times on the selection medium. The presence of the oxalate oxidase gene in *Agrobacterium rhizogenes* is verified by the Southern method, on a preparation of total DNA (lysis of bacteria, purification of the DNA by extraction with the aid of the phenol/chloroform mixture according to the protocol described by Gelvin in the work cited above, cleavage of the purified DNA with the aid of restriction enzymes, electrophoresis on agarose gel, transfer onto a membrane and hybridization according to techniques well known to persons skilled in the art.

c) Obtaining of Transformed Roots and Selection

The transformation is carried out according to the protocol of Guerche et al (1987) and the various culture media, whose composition is presented in table 1 below, are those described by Pelletier et al. (Mol. Gen. Genet., (1983) 191, 244).

Stem segments are removed from the apical end of rape plants (*Brassica napus*: spring varieties Brutor and winter varieties Nickel or Navajo). These segments are surface-sterilized, rinsed in sterile water, cut into segments about 1.5 cm long and placed in a tube containing medium A. Alternatively, the explant used for the transformation may consist of cotyledons collected from approximately eight-day-old young germinations. The inoculation of the end of the segments of scapes, of the hypocotyls or of the petioles of cotyledons is carried out by depositing a suspension of the *Agrobacterium rhizogenes* strain containing the vector pPH100 or the vector p631. Transformed roots appear on the segment of stem or on the petioles of cotyledons after 1 to 2 weeks, they are removed after 3 weeks and placed on agar medium B (15 g/l). These roots contain the T-DNA of the vector pRi specific to *Agrobacterium rhizogenes* alone or accompanied by the T-DNA of the vector carrying the gene encoding oxalate oxidase.

The selection of the transformants containing the T-DNA of the plasmids pPH100 or p631 carrying the gene encoding wheat germin, is carried out according to the following protocol:

the first step consists in removing, with a scalpel, the apical ends (0.5 to 1 cm) of roots cultured preferably in vitro (decontamination or liquid culture stage) or of fragments of leaves of plants cultivated in a greenhouse, and introducing them into 1.5 ml Eppendorf tubes containing 0.5 ml of "oxalate oxidase" reaction mixture (0.015 M Na oxalate in succinate buffer pH 4; 0.05 M). The tubes containing the roots are stored on ice until the sample collection is complete.

the second step is the incubation of the tubes on a water bath at 37° C. for 1 hour, conditions which allow the reaction catalyzed by oxalate oxidase to take place.

the third and final step is the revealing of the hydrogen peroxide produced in the preceding step; the following are successively added to the reaction mixture: a substrate whose oxidation is accompanied by a change in color; this substrate is chosen from phenolic compounds or aromatic amines and, for example, 0.1 ml of 4-chloro-1-naphtol at 0.3% in absolute ethanol and 0.1 ml of peroxidase at 0.006% in 50 mM Tris buffer, pH 7.6. The tubes are stirred and then incubated for at least 2 hours on a water bath at 37° C. A blue color is obtained on the transformed roots, preferably at the level of the apical part and of the stele of the roots. This colored test on the root sample allows the detection of the transformants which have integrated and which express the oxalate oxidase gene.

The solutions of the products used are described below:

Succinate buffer 0.05 M, pH 4, qs 250 ml (store at 4° C., 3 weeks maximum)

3.375 g of Na succinate, adjust to pH 4 with HCl

"Oxalate oxidase" reaction mixture (prepare immediately before use)

18 mg of Na oxalate in 10 ml of succinate buffer

Stock solution 4-chloro-1-naphtol(store at 4° C.)

0.3 g/10 ml absolute ethanol

Working solution of 4-chloro-1-naphtol (prepare immediately before use)

0.1 ml stock solution/10 ml 50 mM Tris; pH 7.6

50 mM Tris buffer; pH 7.6 qs 250 ml (store at 4° C.)

1.96 g Tris-HCl, adjust to pH 7.6 with NaOH

Peroxidase (aliquot and freeze at −20° C.)

6 mg/100 ml 50 mM Tris buffer; pH 7.6 d) Regeneration of Transformed Plants and Phenotypic Sorting

Fragments of selected roots are incubated for 15 days on medium D containing 3 mg/l of 2±4-dichlorophenoxyacetic acid, and then placed on an RCC medium for inducing buds. The rooted plants are then obtained by passages of the buds over the media F and G. The plants are cultivated and self-fertilized to give seeds. The expression of the regenerated plants obtained can be easily checked by simple techniques (squash, blotting, dot or direct staining on fragments of leaves, of stems, and the like). Sorting of the progeny according to the phenotypic characters of the transformed plants makes it possible to eliminate the plants containing the T-DNA of pRi, which exhibit in particular crinkled leaves and shorter internodes. This sorting is then confirmed by methods of molecular analysis.

1-2 Obtaining of Transgenic Cauliflower

According to the same protocol, stem segments are removed from young flowers of *Brassica oleracea* L. var. *Botrytis* cv. Taroke and transformed via the abovementioned *Agrobacterium rhizogenes* A4 strains. The roots expressing the gene encoding oxalate oxidase are selected according to the colored test described and are caused to regenerate for the obtaining of transgenic plants. The regenerated plants obtained are cultured in a greenhouse, vernalized and then self-fertilized and their progeny sorted on the basis of phenotypic characters and of molecular analyses so as to retain only the plants which contain only the T-DNA carrying the oxalate oxidase gene.

1-3 Obtaining of Transgenic Sunflower Calluses

Segments of petioles are collected from 6- to 10-week-old sunflower plants *Helianthus annuus* (variety Euroflor Rustica Prograin Génétique). The segments are disinfected by soaking for 30 minutes in a 1% solution of calcium hypochlorite. The segments of petioles are then placed in a tube containing the Murashige and Skoog agar culture medium. The inoculation of the end of these segments is carried out by depositing a suspension of the *Agrobacterium rhizogenes* strain containing the plasmid pPH100. Transformed roots then appear on the segment of petiole after about 1 month. These roots are removed and placed on agar medium M (appended table 2) supplemented with 6 g/l of agarose.

Selection of the roots expressing the protein with oxalate oxidase activity is carried out at the root stage according to the protocol described above. The roots which are positive to the colorimetric test are then subcultured on the same medium, giving completely transformed calluses which express oxalate oxidase.

1-4 Obtaining of Transgenic Tobacco

The midrib of tobacco leaves is cut into fragments which are placed on a Murashige and Skoog (MS) agar medium. These explants are inoculated with the aid of a suspension of the *A. rhizogenes* strain containing the plasmid pPH100. The roots which appear after a few days are subcultured on the same medium containing 500 mg/l of cefotaxime so as to eliminate the bacterium and then transferred onto a Murashige and Skoog agar medium containing 0.1 mg/l of IAA (3-indolylacetic acid) and 1 mg/l of BAP (6-benzylaminopurine). The buds which form are subcultured on an MS agar medium and the plants obtained transferred into a greenhouse.

1-5 Obtaining of Transgenic Tomato

Tomato plants can be obtained according to the same transformation and selection protocol, starting with roots of transformed plants (Shahin et al, TAG (1986) 72: 770; Morgan et al, Plant Science (1987), 49: 37).

Example 2

Use of this Peroxidase-Based Selection Method for Obtaining Transgenic Plants Expressing a Second Gene of Interest: the Gene Encoding a Protein with Endochitinase Activity 2-1 Obtaining of Transgenic Rape The transformation vector pPH106, comprising the gene encoding wheat germin, derived from the plasmid pPH100 described above, and the chimeric gene encoding an endochitinase activity (WO 92/01792), is obtained according to the method described in patent application WO 94/13790, incorporated by reference.

The preparation of the transformation vector comprises the following steps:

a) Preparation of the Fragment Carrying the Gene Encoding Oxalate Oxidase

The HindIII-EcoRI fragment of about 1420 bp from the plasmid pPH100 cited in section 1-1 of example 1 is purified and recloned into a vector pUC19 according to methods well known to persons skilled in the art. This plasmid is then linearized using the restriction endonuclease EcoRI and the cohesive end is filled with the Klenow fragment. After cutting with the endonuclease HindIII, the HindIII-blunt ended fragment is then purified.

b) Preparation of the Fragment Carrying a Hybrid Gene Encoding a Protein with Endochitinase Activity The HindIII-EcoRI fragment obtained from the plasmid. pBR1 described in patent application WO 92/01792, example 1, incorporated by reference, and containing a chimeric gene encoding a protein with endochitinase activity which comprises the 35S promoter, a sequence encoding a tomato-tobacco hybrid chitinase and the NOS terminator is purified, recloned into the vector pUC19, and then the HindIII site is destroyed in a conventional manner. The blunt ended-EcoR 1 fragment is purified.

c) Preparation of a Vector for Transforming Plants Containing no Kanamycin Resistance Gene The NheI-HindIII fragment comprising the part encoding the kanamycin resistance gene is removed from the T-DNA of the plasmid pBIN19. The use, according to methods well known to persons skilled in the art, of the oligonucleotides CTAGCA and AGCTTG, makes it possible to recircularize the plasmid by recreating the NheI and HindIII restriction sites. The resulting plasmid is then linearized with the restriction endonucleases HindIII and EcoRI.

d) Assembly of the Transformation Vector

The gene encoding oxalate oxidase obtained in a) above and the chimeric gene encoding a protein with chitinase activity (obtained in b) above) were ligated, with the aid of T4 DNA ligase, into a binary vector pBIN19, from which the kanamycin resistance gene, expressed in plants, has been removed (obtained in c) above). The vector obtained, called pPH106, is cloned into the *E. Coli* HB101 strain (Clontech).

The transformation, selection and regeneration steps are carried out according to the protocol provided in the first example.

2-2 Demonstration of the Expression of the Protein of Interest in the Regenerated Transgenic Plants As is described in patent application WO 94/13790, incorporated by reference, techniques for Western blotting and for measuring the chitinolytic activity on crude extracts of proteins of transformed plants make it possible to confirm the correlated expression of endochitinase with that of oxalate oxidase.

The preparation of the crude extracts of proteins of transformed plants is carried out according to the following method: the fragments of tissues (calluses and leaves of plants) were frozen in liquid nitrogen, reduced to a powder and stored at −20° C.

For carrying out electrophoreses, the oxalate oxidase is extracted directly from the plant powder with the Laemmli loading buffer (ref. below).

For the assays of oxalate oxidase activity, the enzymatic extract is obtained by suspending the plant powder in a 0.05 M succinate buffer, pH 4.

For the protein assays, the plant extract, suspended in the above succinate buffer, is centrifuged at 10 000 g for 5 min.

The concentration of the total proteins is determined on the supernatants, called hereinafter crude protein extracts, using the technique of Bradford, Anal. Biochem., (1976), 72, 248–254).

The experiments of Western blotting or of demonstrating the chitinolytic activity use the following protocols:

a) Immunodetection of the Hybrid Chitinase (Western Blotting)

The crude protein extracts are subjected to Western blotting, a technique well known to persons skilled in the art and described by Towbin et al. (Proc. Ntl. Acad. Sci. USA, (1979), 76, 4350-4354), which comprises in particular the following steps:

denaturation by heating at 100° C. for 10 min in a buffer, called loading buffer, consisting of 0.125 M Tris, pH 6.8, 4% SDS, 0.002% bromophenol blue, 20% glycerol, 10% β-mercaptoethanol (according to the protocol described by Laemmli U. K, Nature, (1970), 227, 680–685), followed by centrifugation at 10 000 g;

electrophoretic separation of the various proteins contained in the solubilizate according to the protocol described by Laemmli;

electrotransfer of said proteins contained in the gel onto a PVDF membrane (according to the technique of Towbin et al., ref. above).

The immunodetection is carried out according to the protocol which comprises the following steps:

saturation of the PVDF (polyvinylidene fluoride) membrane onto which the proteins have been transferred by incubating for a minimum of 2 h at 37° C. in a 3% gelatin solution in phosphate-buffered saline containing 0.05% of detergent Tween 20.

incubation (for 1 h at 37° C.) in the presence of the immune serum prepared above (containing the polyclonal antibodies recognizing the recombinant protein), diluted 1/10 000 in phosphate-buffered saline.

3 washes in phosphate-buffered saline containing 0.05% of detergent Tween 20.

The immunodetection of the protein of interest is carried out using an immune serum containing polyclonal antibodies recognizing the hybrid protein with chitinase activity (cf. WO 92/01792 example 5, incorporated by reference).

The antigen-antibody complex is then revealed with the aid of an alkaline phosphatase-conjugated streptavidin-biotin system with the Amersham RPN 23 kit ("Blotting detection kit"), used according to the manufacturer's instructions.

The blot obtained shows, for the leaves of tobacco plants transformed with the plasmid pPH106, the presence of a protein with an apparent molecular weight of about 26±6 kDa, recognized by polyclonal antibodies and absent from the leaves of the control plants. This protein has the same apparent molecular weight as the hybrid protein with chitinase activity described in application WO 92/01792.

b) Demonstration of the Chitinolytic Activity of the Recombinant Protein

The chitinolytic activity of the crude protein extracts of leaves of plants transformed with the plasmid pPH106 and of the crude protein extract of leaves of untransformed plants can be measured according to the following method.

The endochitinase activity of the protein is measured by a radiochemical method which makes it possible to estimate the quantity of monomers or oligomers released by the enzyme from a substrate (tritiated chitin). This method, described by Molano et al. Anal. Biochem., (1977), 83, 648–656), is summarized below.

50 μl of a suspension of tritiated chitin having a specific activity of 0.58 MBq/ml are added to a volume of protein extract of 10 μl. The final volume is adjusted to 300 μl with 0.2 M sodium acetate buffer, pH 5.0.

After incubating for 90 min at 30° C., the chitin hydrolysis reaction is stopped with 100 μl of 20% trichloroacetic acid. The reaction tubes are then centrifuged for 10 min at 12 000 g. An aliquot portion of 100 μl of supernatant containing the soluble oligomers of chitin is collected and the corresponding radioactivity is measured by liquid scintillation in the presence of 5 ml of scintillation mixture. The specific chitinolytic activity is expressed in dpm/μg of protein.

It is observed that the extracts of plants transformed with the plasmid pPH106 have a chitinolytic activity which is significantly higher than that of the extract of control plants. The selection by a calorimetric test therefore makes it possible to obtain plants expressing a gene of interest, in this case the hybrid gene encoding a protein with chitinase activity described in patent application WO 92/01792.

A variant of the recombinant DNA described above may be obtained by replacing the 35S promoter of the cauliflower mosaic virus by the promoter of the *Arabidopsis* EF-1α gene, upstream of one or of the two genes described above.

Transgenic cauliflower, sunflower, tobacco and tomato plants can be obtained according to the same method.

Example 3

Use and Induction of an Inducible Promoter

It is possible to preferentially use a promoter which is inducible in stress situations (for example heat shock, wound, hormonal shock, biotic or abiotic elicitor or bacterial, fungal or viral infection), which is expressed at a sustained level in the various organs and tissues of a plant, in particular the roots and the meristem of a plant.

In this example, the stress-inducible promoter was used which comprises the DNA sequence SEQ ID NO:4 (sequence B preceded by sequence C) or a sequence exhibiting a high degree of homology with this sequence, as described in application WO94/21793, incorporated by reference. This promoter is called hereinafter p246C.

3-1 Preparation of the Transformation Vectors a) Inducible Promoter-Oxalate Oxidase Construction The vector pPH100 described in example 1-1 a) is opened with the aid of the restriction enzymes HindIII and BamHI, and then the fragment of about 13 500 base pairs corresponding to the coding part of oxalate oxidase followed by the NOS terminator in the vector pBIN 19, is purified by agarose gel electrophoresis.

The vector pPH 118 obtained by insertion, according to methods well known to a person skilled in the art, of the stress-inducible promoter p246-C defined above into the plasmid pTZ19R marketed by PHARMACIA, was opened with the aid of the same restriction enzymes. After agarose gel electrophoresis, the HindIII-BamHI fragment of about 1275 bp is isolated and purified. It corresponds to the sequence B preceded by the sequence C of the inducible promoter as are described above and in application WO94/21793.

The ligation of the promoter sequence thus obtained into the above HindIII-BamHI vector places the coding part of the oxalate oxidase under the control of the inducible promoter and of the NOS terminator; the binary vector thus created is called p643. The construction of this vector is illustrated in the appended FIG. I.

3-2 Transformation and Selection

The transformation of rape is carried out according to the protocol described above in example 1-1. The transformed roots expressing the oxalate oxidase gene are selected as described above and left to regenerate. After a hormonal shock, a callus is formed from the roots and produces buds which are then subcultured to give plants. These plants are transferred into a greenhouse after a period of acclimatization.

Tobacco, tomato and cauliflower plants can be obtained according to this same protocol.

Example 4

Selection of the Transformants by a Calorimetric Test on Liquid Medium or Blotting of Dish of Agar Medium or Membrane As oxalate oxidase can diffuse from the site where it is expressed, it is possible to use supports other than the root to carry out the calorimetric test.

4-1. Liquid Medium

The selection of the transformants carrying the gene encoding wheat germin may be carried out directly on the culture medium in vitro after removal of the *agrobacteria*. After having removed the young plants described in point c) of example 1 § 1.1, the "oxalate oxidase" reaction mixture is added to the culture medium or to a sample collected therefrom and then the procedure is carried out as described in example 1 so as to promote the enzymatic reaction and to reveal the products thus obtained.

4-2. Blotting on Membrane a) Sorting of Young Plants

Transgenic rape seeds obtained according to example 1, §1.1, are surface-sterilized and left to germinate in a plastic dish whose bottom is covered with several layers of filter paper and a membrane made of PVDF, Hybond C or cellulose nitrate, which are conventionally used for carrying out Western blottings. The seeds are deposited on the membrane, on a grid which makes it possible to locate their position. The membrane is moistened with sterile water; the dish is then closed and placed in a culture chamber for about eight days. When the roots of the young germinations are 1 to 2 cm long, the plantlets are transferred to another dish, on moistened filter paper, while retaining the position which they had on the membrane.

The membrane is then revealed according to a variant of the protocol described in example 1 § 1.1:

the membrane is incubated at 37° C. for one hour, after having been impregnated with the "oxalate oxidase" reaction mixture (0.015 M Na oxalate in 0.05 M succinate buffer pH 4), the membrane is revealed by addition of the substrate (phenolic compound or aromatic amine) and for example 4-chloro-1-naphthol at 0.03% in absolute ethanol and a solution of peroxidase at 0.0006% in 50 mM Tris-HCl buffer, pH 7.6. This revealing is continued for 2 hours at 37° C.

The blots on the membrane of roots of plants expressing oxalate oxidase are colored blue, which makes it possible to locate the transformants to be preserved.

b) Sorting on Blots Produced From Tissue Sections

Various organs of plants (leaves, petioles, roots, floral pieces and the like) transformed according to the steps described in example 1, are collected. A section is produced with the aid of a scalpel on these fresh samples and the cut surface is firmly applied against the surface of a nitrocellulose membrane. After air-drying for a few minutes, the membrane is revealed as described above.

Example 5

Use of a Promoter Specific to the Seed

The system for immediate revealing on the root is particularly advantageous in the case where the gene of interest is expressed at a late stage of development, as in the seed for example.

5-1 Preparation of the Transformation Vectors

A first vector containing a nucleic sequence encoding a lipase under the control of the *Arabidopsis thaliana* PGEA1 promoter, specific to the seed (Gaubier et al., 1993 cited above) was obtained, according to cloning methods known to persons skilled in the art, from sequences for which information is available in Genbank: the sequence U02622 of 1641 nucleotides encoding a *Geotrichum candidum* lipase 1—strain ATCC 34614 was placed under the control of the *Arabidopsis thaliana* PGEA1 promoter nucleotide sequence (Z11158, 1659 nucleotides) and fused with the Nos terminator, in a plasmid pBluescript.

As described in point d) of example 2 § 2.1, the fragment obtained above was ligated with the aid of the T4 DNA ligase with the gene encoding oxalate oxidase in a binary vector pBIN19 for the transformation step.

5-2 Transformation and Selection

The transformation of rape is carried out according to the protocol described in example 1 with the aid of the vector derived from pBIN19 described above and the selection of the transformants is carried out upon the formation of the roots, according to one of the methods described in example 1 or example 4.

The results show that it is possible, depending on the system for immediate revealing at the root stage of the invention, to select very early transformants which normally express the gene of interest at a late stage of development (seed) or in a vegetative organ other than that on which the selection was carried out.

Tobacco, tomato or cauliflower plants can also be obtained according to a similar protocol.

TABLE 1

Composition of the various media used for obtaining transformed rape plants

| Composition (mg/l) | A | B | D | RCC | F | G |
|---|---|---|---|---|---|---|
| $NH_4NO_3$ | 1650 | | 200 | 1650 | 1650 | 825 |
| $KNO_3$ | 1900 | 2500 | 1250 | 1900 | 1900 | 950 |
| $(NH_4)_2SO_4$ | | 134 | 67 | | | |
| $NaH_2PO_4$ | | 150 | 75 | | | |
| $KH_2PO_4$ | 170 | | 35 | 170 | 170 | 85 |
| $CaCl_2.2H_2O$ | 440 | 750 | 525 | 440 | 440 | 220 |
| $MgSO_4.7H_2O$ | 370 | 250 | 250 | 370 | 370 | 185 |
| $H_3BO_3$ | 12.4 | 3 | 12.4 | 12.4 | 6.2 | 6.2 |
| $MnSO_4.4H_2O$ | 33.6 | 10 | 33.6 | 33.6 | 22.3 | 22.3 |
| $ZnSO_4.7H_2O$ | 21 | 2 | 21 | 21 | 8.6 | 8.6 |
| KI | 1.66 | 0.75 | 1.66 | 1.66 | 0.83 | 0.83 |
| $Na_2MoO_4.2H_2O$ | 0.5 | 0.25 | 0.5 | 0.5 | 0.25 | 0.25 |
| $CuSO_4.5H_2O$ | 0.05 | 0.025 | 0.05 | 0.05 | 0.025 | 0.025 |
| $CoCl_2.6H_2O$ | 0.05 | 0.025 | 0.05 | 0.05 | 0.025 | 0.025 |
| $FeSO_4.7H_2O$ | 22.24 | 27.8 | 27.8 | 27.8 | 27.8 | 22.24 |
| $Na_2EDTA$ | 29.84 | 37.3 | 37.3 | 37.3 | 37.3 | 29.84 |
| Inositol | 100 | 100 | 100 | 100 | 100 | 100 |
| Nicotinic acid | 0.5 | 1 | 1 | 0.5 | 1 | 0.5 |
| Pyridoxine HCl | 0.5 | 1 | 1 | 0.5 | 1 | 0.5 |
| Thiamine | | 10 | 10 | | 10 | |
| Glycine | 2 | | | 2 | | 2 |
| Glucose | 10000 | 20000 | | | | 10000 |
| Sucrose | 10000 | | 20000 | 10000 | 10000 | |
| D-mannitol | | 70000 | | 10000 | | |
| H.A.A. | | 1 | | 1 | 0.1 | 0.01 |
| B.A. | | 1 | | 0.5 | 0.5 | |
| 2,4D | | 0.25 | 3 | | | |
| Adenine sulfate | | | 30 | | | |
| I.P.A. | | | | 0.5 | | |
| GA | | | | 0.02 | | |
| Tween 80 | | 10 | | | | |
| Agar | 8000 | | | 8000 | 8000 | 8000 |
| PH | 5.8 | 5.8 | 5.8 | 5.8 | 5.8 | 5.8 |
| Gentamicin (sulfate) | | 10 | | | | |

NAA: naphthaleneacetic acid
BA: 6-benzylaminopurine acid
2,4D: 2,4-dichlorophenoxyacetic acid
IPA: $N^6$-($\Delta^2$-Isopentenyl)adenine
$GA_3$: gibberellic acid
EDTA: ethylenediaminetetraacetic acid

TABLE 2

Composition of the culture medium M used for culturing the transformed roots of sunflower

| | Composition mg/l |
|---|---|
| $NH_4NO_3$ | 330 |
| $KNO_3$ | 380 |
| $KH_2PO_4$ | 170 |
| $MgSO_4$ | 370 |
| $CaCl_2$ | 440 |
| $H_3BO_3$ | 6.3 |
| $MnSO_4.4H_2O$ | 22.3 |
| $ZnSO_4.7H_2O$ | 1.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |
| Pyridoxine HCl | 0.1 |
| Nicotinic acid | 0.1 |
| Glycine | 0.4 |
| Inositol | 20 |
| Thiamine | 0.02 |
| Sucrose | 30000 |
| Iron citrate | 200 |

The invention claimed is:

1. A method for obtaining transgenic plants, comprising
   (a1) transforming dicotyledonous plant cells or dicotyledonous plant explants with *Agrobacterium rhizogenes* containing two vectors: a vector (i) carrying a T-DNA comprising a DNA sequence encoding an $H_2O_2$ producing protein, and a vector (ii) being the pRi of *Agrobacterium rhizogenes*, in order to obtain transformants, wherein said DNA sequence encoding an $H_2O_2$ producing protein is flanked by elements necessary for expression of said DNA sequence; and wherein said transformation with *Agrobacterium rhizogenes* induces the formation of roots on the transformants; or
   (a2) transforming dicotyledonous plant cells or dicotyledonous plant explants with *Agrobacterium rhizogenes* containing two vectors: a vector (i) containing a recombinant DNA comprising both a DNA sequence encoding an $H_2O_2$ producing protein and a gene encoding a protein of interest, and a vector (ii) being the pRi of *Agrobacterium rhizogenes*, in order to obtain transformants, wherein said DNA sequence encoding the $H_2O_2$ producing protein and said gene encoding a protein of interest are flanked by elements necessary for expression of said genes; and wherein said transformation with *Agrobacterium rhizogenes* induces the formation of roots on the transformants; and
   (b) visually selecting the transformants which express said $H_2O_2$ producing protein by the use of a peroxidase-based colorimetric test, wherein said test is carried out on said transformants in the presence of a substrate for said protein with $H_2O_2$ producing activity and said peroxidase for revealing the formation of $H_2O_2$, and wherein said formation of $H_2O_2$ is revealed by coloration of said transformants, thus leading to selected transformants; and
   (c) regenerating transgenic-plantlets out of said selected transformants and monitoring the expression of said $H_2O_2$ producing protein within said plantlets obtained, wherein said expression is monitored by the use of a peroxidase-based colorimetric test wherein expression of said $H_2O_2$ producing protein is monitored by the presence of $H_2O_2$, revealed by a peroxidase-based colorimetric test; and
   (d) sorting the transgenic plantlets which do not contain said pRi of *Agrobacterium rhizogenes* and optionally carrying out a molecular analysis of the progeny of said sorted plantlets, allowing the selection or the confirmation of the obtainment of transgenic plantlets containing only the DNA sequence encoding said $H_2O_2$ producing protein or the DNA sequence encoding said $H_2O_2$ producing protein and the gene encoding said protein of interest and not the pRi of *Agrobacterium rhizogenes*, wherein said transgenic plantlets containing the pRi of *Agrobacterium rhizogenes* exhibit phenotypic characteristics, such as crinkled leaves and shorter internodes, and transgenic plantlets which do not contain the pRi of *Agrobacterium rhizogenes*, do not exhibit said phenotypic characteristics; and
   (e) generating transgenic plants from said plantlets.

2. The method of claim 1, wherein the transformation according to step (a1) or (a2) induces the formation of roots on the dicotyledonous plant cells or dicotyledonous plant explants; and wherein step
   (b) comprises selecting the roots which express said $H_2O_2$ producing protein by the use of a peroxidase-based colorimetric test on said roots, wherein said test is carried out in the presence of a substrate for said protein with $H_2O_2$ producing activity and peroxidase for revealing the formation of $H_2O_2$, wherein said formation of $H_2O_2$ is revealed by coloration of said roots, thus leading to selected roots; and
   step (c) comprises regenerating transgenic plantlets out of the selected roots and monitoring the expression of said $H_2O_2$ producing protein within said plantlets obtained, wherein said expression is monitored by the use of a peroxidase-based calorimetric test, wherein expression of said $H_2O_2$ producing protein is monitored by presence of $H_2O_2$, revealed by a peroxidase-based colorimetric test; and
   step (d) comprises sorting the transgenic plantlets which do not contain the pRi of *Agrobacterium rhizogenes* and optionally carrying out a molecular analysis of the progeny of said sorted plantlets, allowing the selection or the confirmation of the obtainment of transgenic plants containing only the DNA sequence encoding said $H_2O_2$ producing protein or the DNA sequence encoding said $H_2O_2$ producing protein and the gene encoding said protein of interest and not the pRi of *Agrobacterium rhizogenes*.

3. The method according to claim 1, wherein said calorimetric test in step (b) is carried out on liquid incubation medium after decontamination of the transformed plant cells or plant explants, wherein said decontamination comprises eliminating *agrobacteria* from said liquid medium.

4. The method according to claim 1, wherein said selection in step (b) is carried out in the presence of a saturating concentration of said substrate for said $H_2O_2$ producing protein.

5. The method according to claim 4, wherein the saturating concentration of substrate is from 5 to 50 mM.

6. The method according to claim 1, wherein the calorimetric test in step (c) is carried out on a sample of plant tissue from the plantlets obtained.

7. The method according to claim 1, wherein said plant cells or plant explants are transformed with a vector comprising a recombinant DNA comprising both a DNA sequence encoding an $H_2O_2$ producing protein and a gene encoding a protein of interest, and wherein said gene encoding a protein of interest is a gene of interest which is expressed at a late stage of development of the plant.

8. The method according to claim 1, wherein the plant cells are plant cells obtained from a member selected from the group consisting of rape, cauliflower, sunflower, tomato, and tobacco.

9. The method according to claim 1, wherein the plant cells are cells of the cotyledons, hypocotyls, petioles, or floral scapes.

10. The method according to claim 1, wherein the plant cells do not endogenously produce oxalate oxidase.

11. The method according to claim 1, wherein said plant cells or plant explants are transformed with a vector comprising a recombinant DNA comprising both a DNA sequence encoding an $H_2O_2$ producing protein and a gene encoding a protein of interest, and wherein said protein of interest is an endochitinase.

12. The method of claim 1, wherein said plant cells or plant explants are transformed with a vector comprising a recombinant DNA comprising both a DNA sequence encoding an $H_2O_2$ producing protein and a gene encoding a protein of interest, and further comprising expressing and purifying said protein of interest.

13. The method of claim 1, wherein said elements necessary for the expression of said DNA sequence encoding an $H_2O_2$ producing protein and said gene encoding a protein of interest comprise a promoter, wherein said promoter is selected from the group consisting of the Cauliflower Mosaic Virus (CaMV) $^{35}S$ promoter, the superpromoter chimeric promoter SPP, the rice actin promoter, the barley HMGW promoter, the PCRU radish cruciferin gene promoter, the corn γ-zein gene promoter, the *Arabidopsis* PGEA1 promoter and the *Arabidopsis* PGEA6 promoter.

14. The method of claim 1, wherein said plant cells or plant explants are transformed with a vector comprising a recombinant DNA comprising both a DNA sequence encoding an $H_2O_2$ producing protein and a gene encoding a protein of interest, and wherein the expression of said gene encoding a protein of interest confers resistance to disease caused by an organism selected from the group consisting of fungi, bacteria, arthropods and nematodes.

15. The method of claim 1, wherein said plant cells or plant explants are transformed with a vector comprising a recombinant DNA comprising both a DNA sequence encoding an $H_2O_2$ producing protein and a gene encoding a protein of interest, and wherein said gene encoding a protein of interest encodes a protein of agronomic or industrial interest.

16. The method of claim 1, wherein said plant cells or plant explants are transformed with a vector comprising a recombinant DNA comprising both a DNA sequence encoding an $H_2O_2$ producing protein and a gene encoding a protein of interest, and wherein said gene encoding a protein of interest encodes a protein conferring resistance to pathogenic agents.

17. The method according to claim 1, wherein said $H_2O_2$ producing protein is an oxalate oxidase protein.

18. The method according to claim 1, wherein said $H_2O_2$ producing protein is wheat germ protein.

* * * * *